(12) United States Patent
Rashidi

(10) Patent No.: US 7,218,958 B2
(45) Date of Patent: May 15, 2007

(54) ELECTROPHYSIOLOGY/ABLATION CATHETER HAVING SECOND PASSAGE

(75) Inventor: Rassoll Rashidi, Lakewood, OH (US)

(73) Assignee: St. Jude Medical, Atrial Fibrillation Division, Inc., Maple Grove, MN (US)

( * ) Notice: Subject to any disclaimer, the term of this patent is extended or adjusted under 35 U.S.C. 154(b) by 339 days.

(21) Appl. No.: 10/784,512

(22) Filed: Feb. 23, 2004

(65) Prior Publication Data

US 2005/0187456 A1  Aug. 25, 2005

(51) Int. Cl.
  *A61B 5/04* (2006.01)
  *A61B 18/14* (2006.01)
(52) U.S. Cl. .......................... 600/374; 600/381; 606/41
(58) Field of Classification Search ................ 600/374, 600/381; 606/41
  See application file for complete search history.

(56) References Cited

U.S. PATENT DOCUMENTS 4,559,951 A * 12/1985 Dahl et al. .................. 600/374
5,552,713 A    9/1996  Rashidi
5,861,024 A    1/1999  Rashidi
6,325,797 B1  12/2001  Stewart et al.
2002/0065514 A1  5/2002  Rashidi
2003/0109778 A1  6/2003  Rashidi
2004/0215139 A1* 10/2004  Cohen .......................... 606/34

* cited by examiner

*Primary Examiner*—Lee S. Cohen
(74) *Attorney, Agent, or Firm*—Wiley Rein LLP

(57) ABSTRACT

A deflectable tip cardiac electrophysiology/ablation lumen catheter includes first and second passages, one of which communicates with an inflatable member or balloon. The second passage terminates in an opening or port downstream of the inflatable member. The second passage is adapted to introduce a liquid during an electrophysiology study while the inflatable member prevents backflow of an injected liquid or dye and blood, or is adapted to alternatively receive a guide wire therethrough.

13 Claims, 5 Drawing Sheets

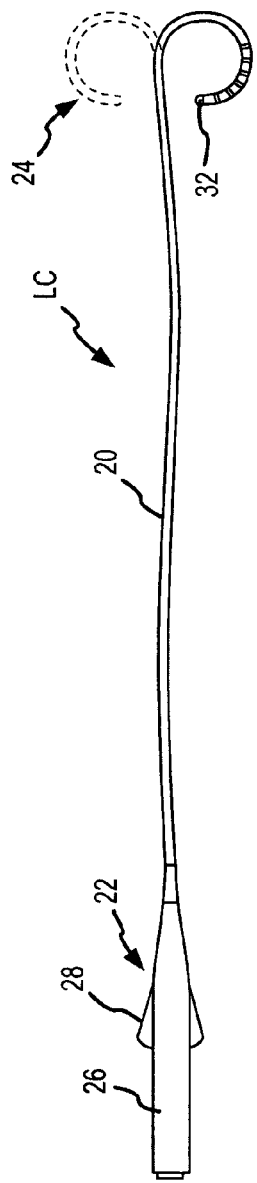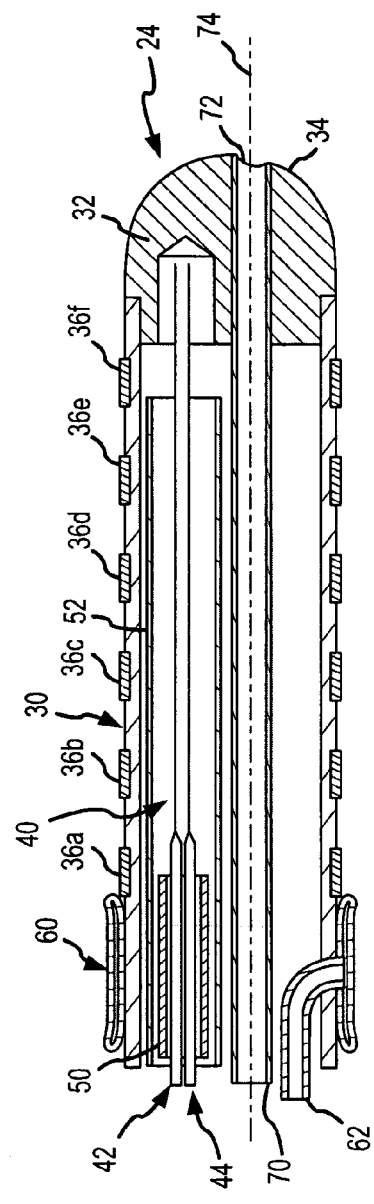
FIG.1
FIG.2

ELECTROPHYSIOLOGY/ABLATION CATHETER HAVING SECOND PASSAGE

BACKGROUND OF INVENTION

The present invention relates to catheters employed for diagnostic and/or therapeutic procedures in medicine, more specifically in minimally invasive cardiac electrophysiology studies and/or cardiac ablation procedures.

It is known from the inventors' prior patents and pending applications to provide a pair of tension and compression members (such as push/pull wires) that cooperate to selectively actuate a distal end of a catheter. The distal end typically carries axially-spaced electrodes which, when located in the body passage such as the heart, monitor and record intra-cardiac electrical signals during desired studies or intracardiac mapping procedure. As is known, the electrodes conduct the cardiac electrical signals to monitoring and recording devices. In addition, the electrodes may be used to deliver electrical energy to selectively destroy a site of cardiac tissue that causes an arrhythmia or abnormality in the heart rhythm.

It is important for these types of procedures that wires extending through the catheter for connection with the electrode be of sufficient size to carry desired electrical energy levels to perform these procedures. It is also important that a distal portion of the catheter be able to deflect into a variety of configurations, typically curved configurations having selective radii of curvature in response to actuation from a catheter handle. U.S. Pat. Nos. 5,552,713 and 5,861,024 are commonly owned by the assignee of the present application and show and describe in detail preferred catheter embodiments of this type. The disclosure and details of these patents are expressly incorporated herein by reference. The actuating mechanism described in the patents is ergonomic, easy to operate, requires a relatively low force to form a desired curvature of the catheter distal portion, allows a comfortable range of displacement of the actuator to provide a full range of curvature formation of the catheter distal portion, and permits for curvature formation and curvature retention by a single action of the physician's hand. These desired features are all achieved through side-by-side longitudinal reciprocation of tension/compression members that cooperate to provide simultaneous tension in one member or wire, and compression in the other member or wire. The tension/compression members preferably have a generally circular cross-section throughout a major portion of their length and a generally flattened, ribbon-like configurations adjacent the distal portion of the catheter. A kinematic junction is provided on the ribbon-like portions of the tension/compression members. Bi-directional curvature or lateral deflection is thus provided by employing tension/compression members without the need of a compression strut in the distal portion. Typical dimensions of a catheter casing, electrodes, and diametrical curvature upon actuation are set forth in greater detail in commonly owned U.S. patent application Ser. No. 09/726,235, (Publication No. US-2002-0065514-A1, published May 30, 2002), the details of which are also incorporated herein by reference.

It is known from U.S. Pat. No. 6,325,797 to use an inflatable balloon that is selectively pressurized from an associated liquid source. A lumen is formed within the catheter and carries the liquid, such as saline, to the balloon. In this manner, the balloon is selectively inflated to engage the inner wall of an intracardiac vessel, for example the pulmonary vein wall.

However, a need exists for an electrophysiology lumen catheter that provides effective minimally invasive cardiac diagnostic electrophysiology and/or cardiac ablation procedures, that also provides a flexible liquid delivery tube within the shaft of the catheter, and still maintains all of the benefits of bi-directional deflection and curvature configurations.

SUMMARY OF INVENTION

An electrophysiology/ablation catheter includes a casing having a proximal end and at least one electrode adjacent a distal end thereof. A deflection mechanism or assembly is provided in the casing for selectively deflecting the distal end of the catheter. An electrical lead is connected to each of the electrodes and extends through the tubular casing. An actuator disposed adjacent the proximal end of the catheter deflection assembly is operative to laterally deflect the distal end of the catheter. An inflatable member extends from an outer surface of the casing when inflated and is supplied with an associated fluid through a first passage through the casing. A second passage communicates with an opening in the casing that is located on the distal end side of the inflatable member.

A distal end of the second passage terminates at a distal tip of the catheter in a first embodiment.

In a second embodiment of the invention, the distal end of the second passage terminates at a location between the distal tip of the catheter and the inflatable member.

The balloon is selectively inflated to assume a preferably generally annular shape and prevents back-flow of an injected liquid such as a dye and blood during an electrophysiology study.

The second passage is used to deliver liquid into the cavity of the heart during cardiac electrophysiology studies, and may also advantageously be used as a passage for placement of a guide wire into a desired site within the heart cavity.

A primary advantage of the present invention is the ability to combine these various features into a single catheter assembly.

Yet another advantage is the capability of incorporating the inflatable balloon functions in conjunction with a secondary passage for liquid delivery and without impacting the deflection capabilities of the electrophysiology catheter.

A further advantage of the invention relates to alternative use of the liquid delivery passage for placement of a guide wire into a desired heart cavity site.

Still other advantages and benefits of the invention will become apparent to those skilled in the art upon reading and understanding the following detailed description.

BRIEF DESCRIPTION OF DRAWINGS

FIG. 1 is a view of the cardiac catheter of the present invention.

FIG. 2 is an enlarged cross-sectional view of a distal end of a first embodiment of the catheter with an inflatable member in a deflated state.

DETAILED DESCRIPTION OF THE INVENTION

Figure 3:
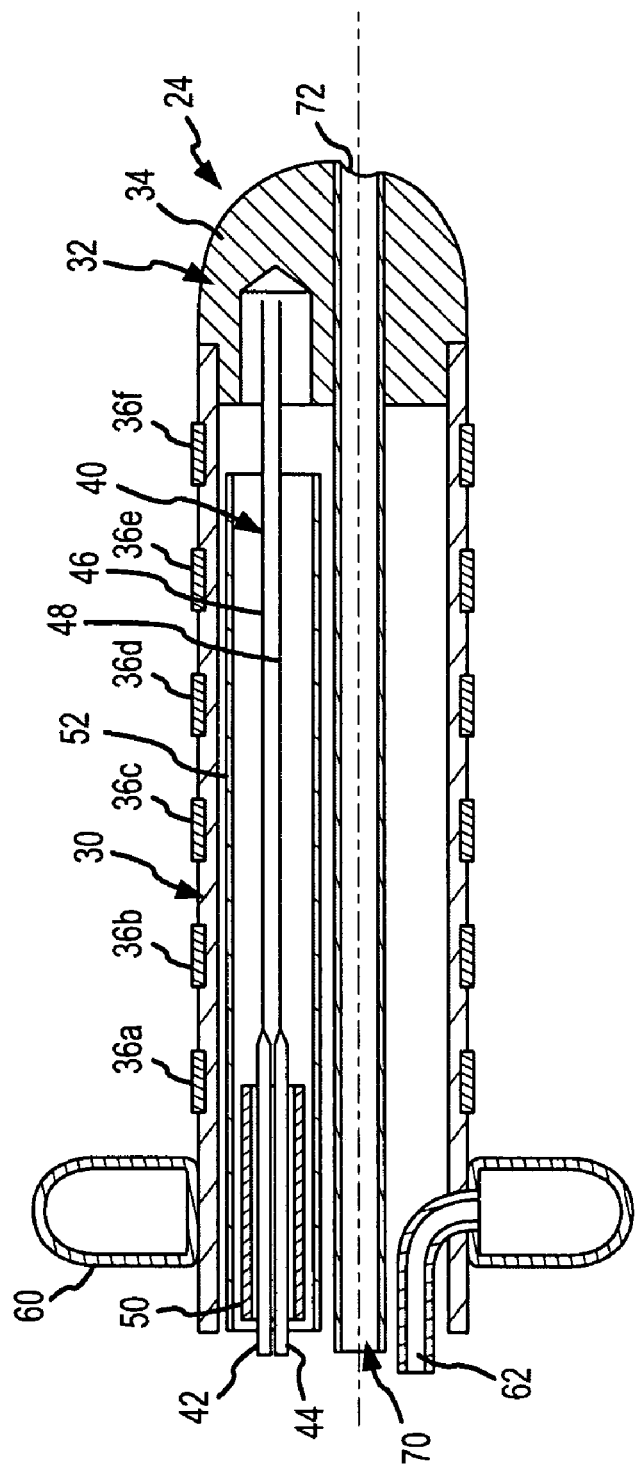
FIG. 3 is a view similar to FIG. 2 with the inflatable member shown in an inflated state.

FIG. 1 illustrates an electrophysiology lumen catheter LC, and the drawings thereof are not intended to limit the invention. The lumen catheter assembly LC includes an elongated flexible main casing or body 20 that includes an actuator assembly 22 at one end and a distal portion 24 at the other end. Although the details are not shown in FIG. 1, it is also contemplated that the catheter assembly can include two main components, a blood-contacting portion and a sub-assembly that includes the actuator mechanism as shown and described in commonly owned U.S. Pat. No. 5,861,024. The actuator mechanism 22 preferably includes a handle 26 and a delta-shaped (Δ-shaped) actuating member 28 that is selectively manipulated by the user to cause desired deflection or curvature of the distal portion 24 of the catheter assembly. Again, although this particular arrangement of the actuator mechanism and deflectable distal portion are shown and described in the commonly owned prior patents, it will also be appreciated that selective modifications can be made without departing from the scope and intent of the present invention.

With continued reference to FIG. 1, and additional reference to FIGS. 2 and 3, a first embodiment of the lumen catheter assembly LC will be described in greater detail. Particularly, the distal portion 24 includes an outer body 30, typically a tubular outer body, that is secured to or receives a distal electrode 32 which is shown as a generally mushroom-shaped configuration. That is, the distal electrode 32 has a hemispherical dome portion 34 that closes the end of the body. In addition, axially spaced electrodes 36a–f are provided along the body 30 and are each connected to a separate electrical wire (not shown for ease of illustration) that conducts electrical energy to the respective electrode in a manner generally well-known in the art for diagnostic and therapeutic procedures.

The distal portion of the catheter is selectively deflected by a catheter deflection assembly. The deflection assembly includes a pair of tension and compression members 40 which acts in concert to selectively deflect the distal end, preferably in a curved configuration (FIG. 1). As particularly illustrated in FIG. 2, the tension/compression member pair 40 includes a first member 42 and a second member 44 disposed in side-by-side relation. The tension/compression members are disposed in side-by-side relation within an inner tube 50 which extends to the proximal end of the catheter (not shown). Additionally, a thin wall polymer tube 52 is received over the flattened ribbon-like portions of the tension/compression members in order to prevent lateral separation of these components during actuation and/or curvature formation. Accordingly, the tube 52 terminates at the location shown in FIG. 2 and does not extend to the proximal end like the inner tube 50. The tension/compression members are typically arranged to provide curved deflection in either direction as represented in phantom in FIG. 1. The tension/compression members are preferably thin wires (e.g., stainless steel wires) received in the tube 50, and include the flattened or ribbon-like portions 46, 48. Again, particular details of the deflection assembly are shown and described in the commonly assigned patents and applications noted above.

An annular inflatable member such as balloon 60 communicates through a first passage 62 with a source of liquid such as saline. It will be understood that the passage 62 extends through the length of the catheter body and is in operative communication with a liquid source (not shown). As shown in FIG. 2, the annular balloon is disposed on the outer surface of the body 30 and is shown in a deflated condition. Upon introduction of a liquid into the balloon, the balloon inflates to an expanded state or condition (FIG. 3) thereby engaging an inner wall of the body passage and providing a sealed arrangement therewith. The inflatable member is preferably disposed at a predetermined dimension from the terminal end of the distal portion and likewise at a location where the electrodes are interposed between the balloon and the distal tip of the catheter. As will be appreciated, the particular location of the balloon may be varied as desired for particular electrophysiology studies.

Also extending through the body 20 of FIG. 1 is a second lumen or passage 70. The second passage is dimensioned to serve as a liquid or dye delivery tube and also advantageously is dimensioned to alternatively receive a guide wire therethrough for reasons which will be described in greater detail below. The second passage or lumen 70, for example, may have an inner diameter of approximately 0.037 inches, adapting it to receive a guide wire on the order of 0.035 inches. These dimensions are merely for exemplary purposes and should not be deemed limiting, since other dimensions can be used with equal success. The second passage 70 extends the length of the catheter body 20 and preferably terminates at the distal end. As shown in FIGS. 2 and 3, the terminal end or port 72 of this passage is located at the distal tip within the hemispherical dome portion 32. That is, a guide wire, represented herein by dotted line 74, can proceed through the second lumen and facilitates guiding of the distal end of the catheter to a desired location within the body cavity. Thus, it is desirable in this instance that the lumen 70 terminate at the distal tip.

Figure 4:
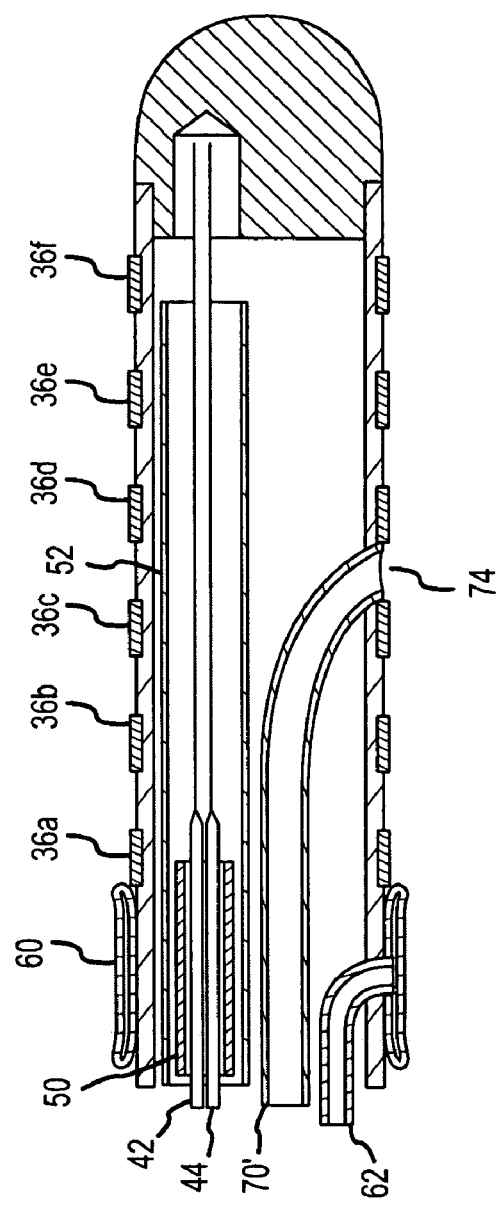
FIG. 4 is an enlarged detail cross-sectional view of a second embodiment of a distal end of the catheter with the inflatable member in a deflated state.
Figure 5:
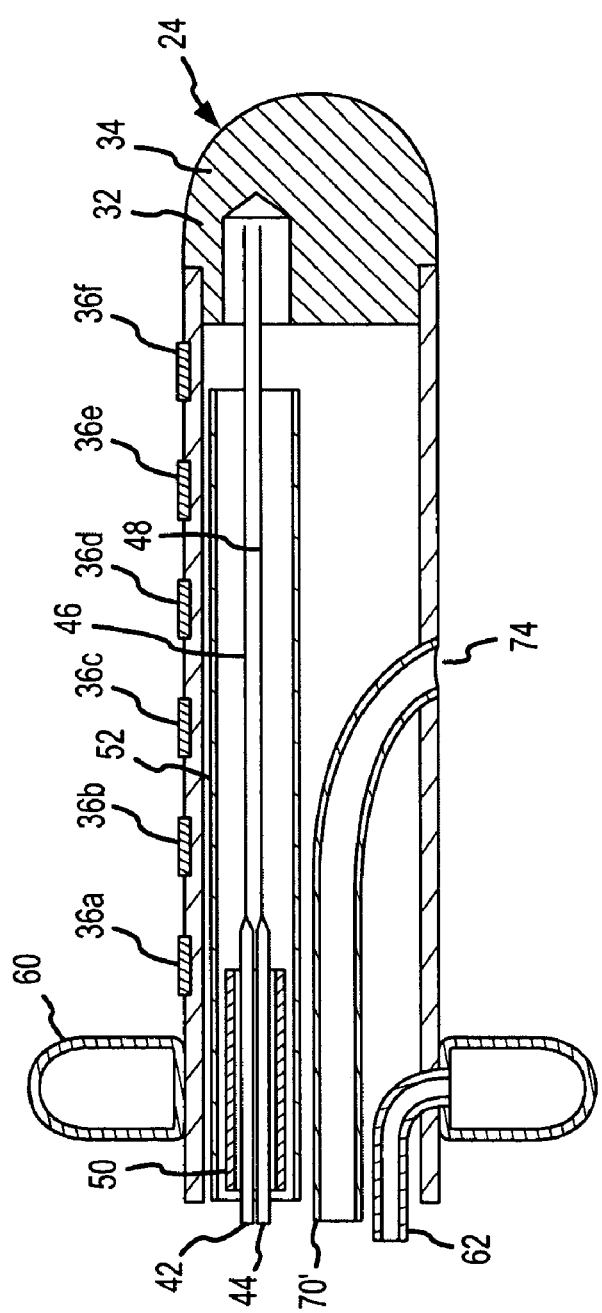
FIG. 5 is a view of the distal portion of the catheter of FIG. 4 with the inflatable member in an inflated state.

This arrangement of the second lumen may be compared to that shown in FIGS. 4 and 5 where like reference numerals with a primed suffix refer to like elements, and new reference numerals refer to new elements. The primary distinction is the location of the terminal end or port of the second passage 70'. Here, the terminal end 74 is located at or extends through a sidewall of the outer body 30. As will be appreciated from FIGS. 4 and 5, the terminal location 74 of the second passage is preferably located between the distal tip and the inflatable member. In this manner, when the balloon is inflated as shown in FIG. 5, the second passage delivers a liquid or dye to a location disposed between the inflated balloon and the distal tip of the catheter. Even though the terminal end of the second passage is not located at the distal tip of the catheter, and may not be as desirable for use as a through passage that receives a guide wire, the embodiment of FIGS. 4 and 5 still provides the advantageous function of a delivery tube through which a liquid or dye can be introduced downstream of the sealed area provided by the inflated balloon (and that is selectively inflated via the first passage 62).

Figure 6:
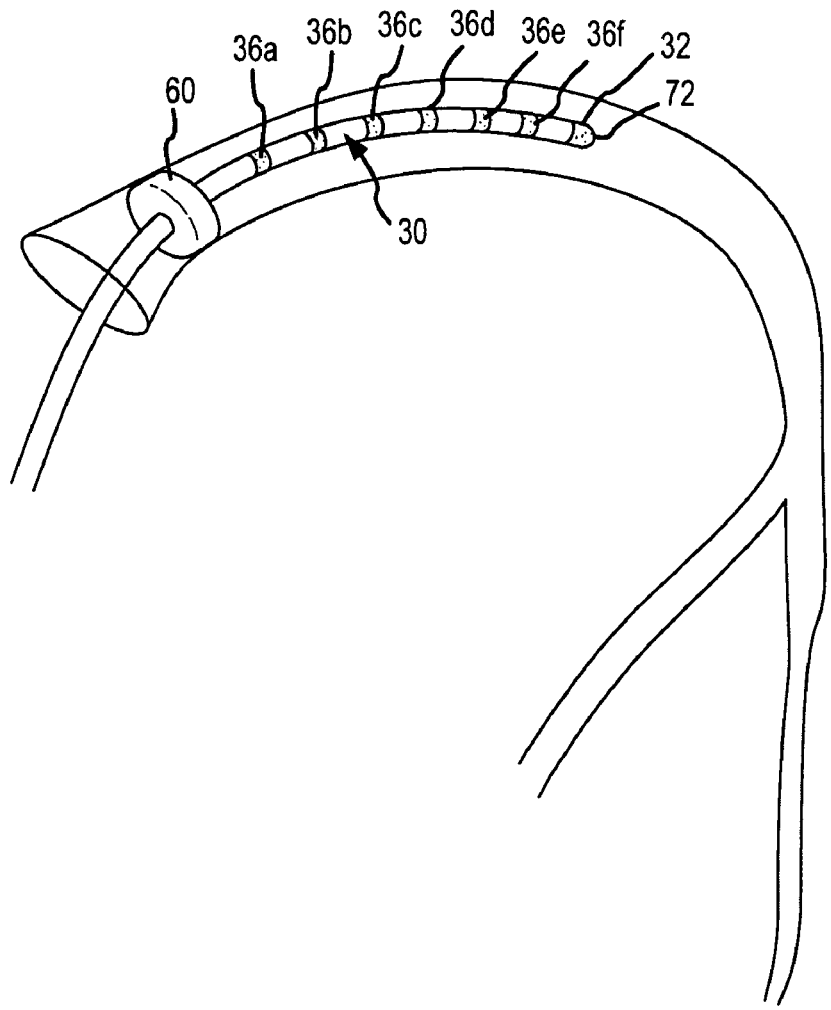
FIG. 6 is a schematic view of the distal portion of the lumen catheter with the inflatable member in an inflated state and liquid being discharged from a port located in the distal end.

As shown in FIG. 6, the distal end of the catheter of FIG. 1 is shown inserted into a cardiac cavity, for example, the coronary sinus. The opening in the coronary sinus is illustrated as a generally conically tapered arrangement. The balloon is inflated into engagement with an interior wall of the coronary sinus passage via a liquid provided through the first passage and fluid is able to be discharged from an end port, whether at the distal end or at another location downstream of the inflated balloon via the second passage, so that the lumen catheter introduces an injected liquid or dye during an electrophysiology study.

In summary, the actuator is still able to alter the configuration of the catheter and the arrangement provides a flexible liquid delivery tube disposed within the catheter shaft. The tip steering mechanism within the catheter handle and distal portion steerability and configuration, along with the electrical features are still retained, while adding the ability to deliver liquid to the cavity of, for example, the heart during cardiac electrophysiology studies. The same second tube may be advantageously used as a passage for placement of a guide wire into a desired site within, for example, the heart cavity. The distal, open end of the secondary passage either exits or terminates at the distal tip of the catheter or at the proximity of the distal tip.

Provision of an inflatable balloon disposed externally and circumferentially in an axi-symmetric configuration on the outer surface of the catheter shaft is provided proximal to the last electrode. Saline or other appropriate liquid may be used to inflate the balloon. The balloon, upon inflation, assumes a preferred annular or donut-shaped configuration. A second flexible tube disposed within the shaft of the catheter has its distal end exiting the catheter outer body and terminating for communication with the interior of the balloon. This allows a second liquid to be introduced into the cavity or to receive a guidewire therethrough.

When the distal portion of the catheter is placed into a typical cardiac vessel for example the coronary sinus, the balloon is inflated in order to prevent backflow of the injected liquid or dye and blood during the electrophysiology study.

Both of the elongated flexible tubes or lumens described above are terminated at the proximal end of the catheter handle with appropriate inlet openings. The openings are used to deliver liquid into each of the tubes as required. When the liquid delivery tube is alternatively used as a passage for guide wire placement, the guide wire can be introduced into this tube via its inlet opening, positioned at the proximal end of the catheter. Once the catheter distal end is positioned in place, the guidewire is then removed and the lumen can be used to introduce a liquid into the body cavity.

The invention has been described with reference to the preferred embodiments. Obviously, modifications and alterations will occur to others upon a reading and understanding of this specification. The invention is intended to include all such modifications and alterations insofar as they come within the scope of the appended claims or the equivalents thereof.

Having thus described the invention, it is now claimed:

1. An electrophysiology/ablation lumen catheter comprising:
   a) an elongated flexible body having a central lumen, a proximal end and at least one electrode disposed adjacent a distal end thereof;
   b) a catheter deflection assembly disposed in the body;
   c) an electrical lead connected to each of the electrodes and extending through the body to adjacent the proximal end thereof, the lead adapted for external connection thereof;
   d) an actuator connected adjacent the proximal end of the catheter deflection assembly and operable upon movement to effect lateral displacement of the distal end;
   e) an inflatable member operatively extending from an outer surface of the body when inflated;
   f) a first passage extending through the body within said central lumen and adapted to supply an associated liquid therethrough to the inflatable member; and
   g) a second passage within said central lumen that communicates with an opening in the body located on the distal end side of the inflatable member, wherein the opening is located inwardly from a terminus of the distal end in a sidewall of said body.

2. The lumen catheter of claim 1 wherein the second passage is adapted to convey an associated fluid from the proximal end of the catheter to the distal end and into an associated body cavity.

3. The lumen catheter of claim 1 wherein the catheter deflection assembly includes a pair of tension/compression members extending through the body.

4. The lumen catheter of claim 3 wherein the catheter deflection assembly moves the distal end in a plane substantially normal to a longitudinal extent of the catheter.

5. The lumen catheter of claim 3 wherein tensioning of one of said pairs of tension/compression members and simultaneously compressing the other of the tension/compression members deflects the catheter.

6. The lumen catheter of claim 5 wherein the tension/compression members are disposed in side-by-side relationship.

7. The lumen catheter of claim 5 wherein said pair of tension/compression members each have a portion thereof adjacent the distal end formed to have a flattened transverse section with the balance thereof circular.

8. The lumen catheter of claim 1 wherein the opening is axially located between a terminus of the distal end and the inflatable member.

9. The lumen catheter of claim 1 wherein the second passage is dimensioned to receive a guidewire therethrough.

10. An electrophysiology/ablation lumen catheter comprising:
    a) an elongated flexible body having a central lumen, a proximal end and a series of spaced electrodes disposed adjacent a distal end thereof;
    b) a pair of tension/compression members extending through the body for selectively deflecting at least the distal end of the body;
    c) an electrical lead connected to each of the electrodes and extending through the body to adjacent the proximal end thereof, the leads adapted for external connection thereof;
    d) an actuator operatively connected to the tension/compression members and operable upon movement to effect lateral displacement of the distal end;
    e) an inflatable member operatively extending from an outer surface of the body when inflated;
    f) a first passage extending through the body within said central lumen and adapted to supply an associated liquid therethrough to the inflatable member; and
    g) a second passage within said central lumen that communicates with an opening in the body located on the distal end side of the inflatable member, wherein the opening is located inwardly from a terminus of the distal end in a sidewall of said body.

11. The lumen catheter of claim 10 wherein the second passage is adapted to convey an associated fluid from the proximal end of the catheter to the distal end and into an associated body cavity.

12. The lumen catheter of claim 10 wherein the opening is axially located between a terminus of the distal end and the inflatable member.

13. The lumen catheter of claim 10 wherein the second passage is dimensioned to receive a guidewire therethrough.

* * * * *